United States Patent [19]

Moreau et al.

[11] 4,211,776
[45] Jul. 8, 1980

[54] N-SUBSTITUTED 2-METHOXYBENZENESULPHONAMIDES, PROCESS FOR PREPARING THEM AND MEDICAMENTS CONTAINING THEM

[75] Inventors: Robert C. Moreau, Clichy; Jean-Paul Fournier, Paris, both of France

[73] Assignee: Choay S.A., Paris, France

[21] Appl. No.: 947,623

[22] Filed: Oct. 2, 1978

Related U.S. Application Data

[62] Division of Ser. No. 693,896, Jun. 8, 1976, Pat. No. 4,132,786.

[30] Foreign Application Priority Data

Jun. 9, 1975 [FR] France .................. 75 17973

[51] Int. Cl.² .................. A61K 31/32; A61K 31/40; C07D 207/00; C07D 209/00
[52] U.S. Cl. .................. 424/228; 260/313.1; 260/397.7 R; 424/248.52; 424/267; 424/274; 544/106; 546/246
[58] Field of Search .................. 424/228, 248.52, 267, 424/274; 260/397.7, 313.1; 544/106; 546/246

[56] References Cited

U.S. PATENT DOCUMENTS

| | | | |
|---|---|---|---|
| 3,060,206 | 10/1962 | Novello | 260/397.7 |
| 3,139,381 | 6/1964 | Novello | 424/228 |
| 3,444,177 | 5/1969 | Schmidt et al. | 544/106 |
| 3,580,949 | 5/1971 | Gruenman et al. | 260/397.7 |
| 3,840,569 | 10/1974 | Beck | 260/397.7 |
| 4,113,463 | 9/1978 | Oshio et al. | 260/397.7 |

OTHER PUBLICATIONS

Chem. Abst. 64, 12664(h)(1966).
Chem. Abst. 69, 77246(s)(1968)—Croce et al.
Chem. Abst. 69, 86983(g)(1968)—Lindquist et al.

*Primary Examiner*—Douglas W. Robinson
*Attorney, Agent, or Firm*—Weiser, Stapler & Spivak

[57] ABSTRACT

The invention relates to new N-substituted benzenesulphonamides of general formula

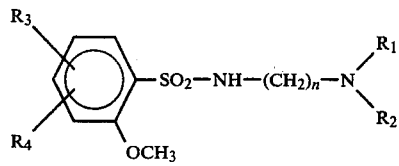

in which
  n is 2 or 3,
  $R_1$ and $R_2$ are hydrogen atoms, methyl, ethyl groups, or jointly form with the nitrogen a nitrogenized heterocyclic ring having 5 or 6 members, in particular a piperidino, pyrrolidino or morpholino group.
  $R_3$ is a hydrogen atom, an $NO_2$ group, an $NH_2$ group, or a halogen,
  $R_4$ is a hydrogen, a halogen, $NH_2$ group or a sulphonamide group.

These compounds are useful as active substances of medicaments, in particular as antiemetic.

18 Claims, No Drawings

N-SUBSTITUTED 2-METHOXYBENZENESULPHONAMIDES, PROCESS FOR PREPARING THEM AND MEDICAMENTS CONTAINING THEM

The present application is a divisional of U.S. Ser. No. 693,896, filed June 8, 1976, now U.S. Pat. No. 4,132,786.

The invention relates to new N-substituted benzenesulphonamides, the processes for preparing them and the medicaments containing them.

The N-substituted benzenesulphonamides of the present invention are substituted in the benzene ring in 2 position by a methoxyl group and correspond to the general formula

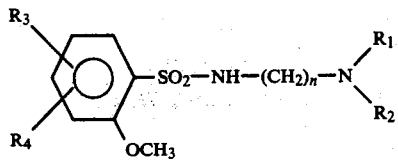

in which
n is 2 or 3,
$R_1$ and $R_2$ are hydrogen atoms, methyl, ethyl groups, or jointly form with the nitrogen a nitrogenized heterocyclic ring having 5 or 6 members, in particular a piperidino, pyrrolidino or morpholino group,
$R_3$ is a hydrogen atom, an $NO_2$ group, an $NH_2$ group, or a halogen,
$R_4$ is a hydrogen, a halogen or a sulphonamide group.

The invention also relates to the addition salts of these N-substituted 2-methoxybenzenesulphonamides, in particular with physiologically tolerable mineral or organic acids.

Among the N-substituted 2-methoxybenzenesulphonamides of the invention, preferred compounds are those of the general formula

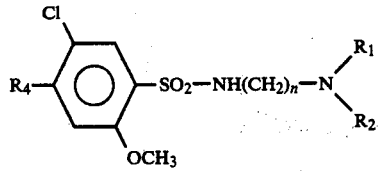

in which
n is 2 or 3,
$R_1$ and $R_2$ are methyl or ethyl groups,
$R_4$ is a hydrogen or an $NH_2$ group.

Particularly interesting compounds are those corresponding to the following formulae

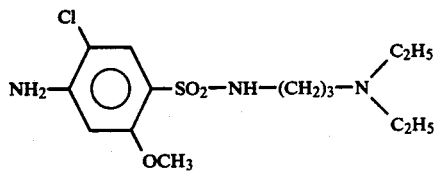

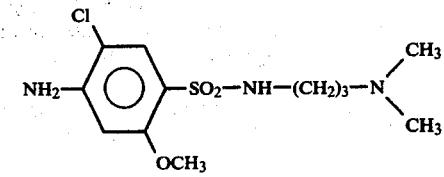

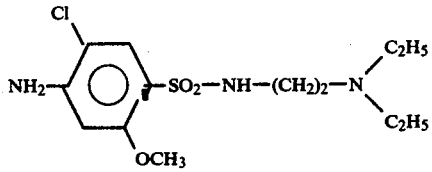

The invention also relates to 2-methoxybenzenesulphonyl chlorides of the formula

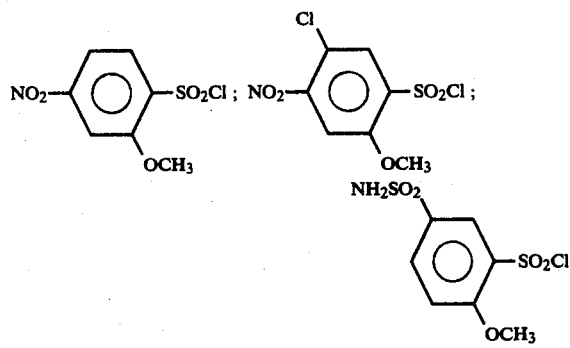

A general method of preparing the N-substituted 2-methoxybenzenesulphonamides of Formula I consists in preparing a 2-methoxybenzenesulphonyl chloride of the formula

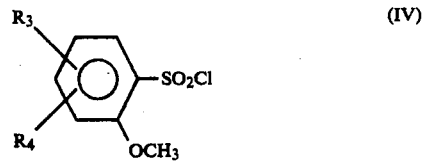

in which
$R_3$ and $R_4$ have the significances hereinbefore indicated, and in reacting this sulphonyl chloride (IV) with an amine corresponding to the general formula

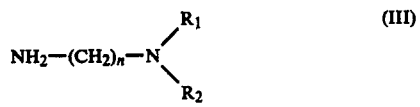

in which
$R_1$ and $R_2$ have the significances hereinbefore indicated.

The 2-methoxybenzenesulphonyl chlorides (IV) may be obtained generally speaking from the corresponding aryl amine by operating in the following manner:

(a) The diazonium salt is formed from the aryl amine, in particular by reacting the amine in solution in hydrochloric acid with a solution of nitrite of an alkali metal, the reaction mixture being held at a temperature below 10° C.

(b) The diazonium salt obtained in this way is reacted in solution with sulphur dioxide. Preferably, operation is carried out in the presence of acetic acid and a catalyst, in particular a copper-based catalyst (modified Sandmeyer reaction).

The complete reaction diagram of the preparation of the benzenesulphonamides of the invention is therefore as follows:

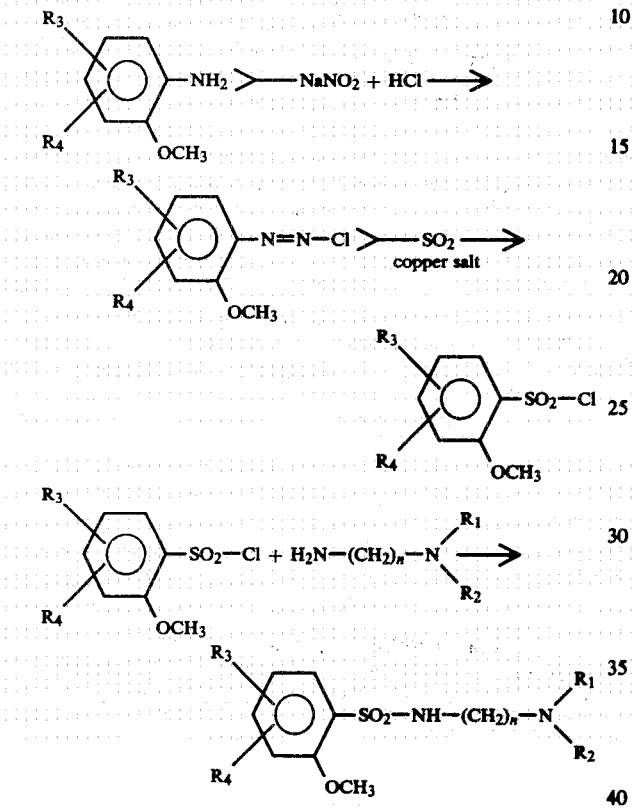

Preferred aryl amines for the preparation of the benzenesulphonyl chlorides are:
2-aminoanisole,
2-methoxy-4-nitroaniline
2-amino-4-chloro-5-nitroanisole,
2-amino-4-chloroanisole,
2-nitroanisole.

Preferred amines for the preparation of the N-substituted 2-methoxybenzenesulphonamides (I) by reaction with a benzenesulphonyl chloride are:
dimethylaminoethylamine,
dimethylaminopropylamine,
diethylaminoethylamine,
diethylaminopropylamine,
piperidinopropylamine,
morpholinoethylamine,
morpholinopropylamine,
pyrrolidinoethylamine.

The following Examples illustrate, in a detailed manner, methods of preparing compounds according to the invention.

EXAMPLE 1

Preparation of 2-methoxybenzenesulphonyl chloride.

0.25 mol (30.8 g) of 2-aminoanisole in solution in 25 ml of acetic acid is placed in a 500 ml three-necked flask equipped with a stirring system, a thermometer and a dropping funnel. 55 ml of hydrochloric acid are added in small portions (d=1.18). The amine is diazotized at −5° C. by adding 19 g of sodium nitrite in solution in 45 ml of water.

Moreover, to 150 ml of pure acetic acid there are added 12 g of cupric chloride dissolved in a sufficient quantity of water and the solution is saturated in the cold state with sulphur dioxide.

The freshly prepared diazonium salt is poured slowly into the acetic solution while stirring well. The mixture is heated to between 50° and 60° C. under a stream of sulphur dioxide for 4 hours.

The solution is poured over crushed ice and the sulphonyl chloride is then extracted with three portions of 50 ml of chloroform. The organic phase is dried, filtered and then evaporated under reduced pressure. Fractional distillation under vacuum (vane pump) of the oil obtained enables two fractions to be isolated:
the first is constituted by 2-chloroanisole;
B.p. 84° C. at 13 mm Hg Yield=35%
the second is constituted by the 2-methoxybenzenesulphonyl chloride;
B.p. 120° C. at 0.1 mm Hg (literature 126–9 at 0.3 mm)
M.p.=50° C.
Yield=30%

Preparation of the N-substituted 2-methoxybenzenesulphonamides

General Method of operation:

0.01 mol of 2-methoxybenzenesulphonyl chloride is dissolved in 20 ml of chloroform; 0.01 mol of the chosen amine in solution in 10 ml of chloroform is added drop by drop; the solutions are left in contact for two hours.

The mixture is evaporated to dryness; 50 ml of water are added to the solid obtained and washing is carried out with two portions of 10 ml of ethyl ether. The aqueous phase is alkalized with a sufficient quantity of a solution of potassium hydroxide (d=1.38) until the precipitate formed is redissolved. The solution is washed with two portions of 10 ml of ethyl ether and then hydrochloric acid is added drop by drop until a precipitate is formed (pH slightly alkaline), which is extracted with two portions of 30 ml of ethyl ether or chloroform. The organic phase is dried, filtered and then evaporated under reduced pressure. The basic sulphonamide is obtained in an oily or crystallized form.

Yield: 59 to 70% according to the amines.

By adding a saturated alcoholic solution of picric acid, the picrates of the benzenesulphonamides are obtained; they are crystallized in absolute ethanol at boiling point.

Examples of N-substituted 2-methoxybenzenesulphonamides prepared by the process hereinbefore described are given in the following Table. These compounds have a general structure corresponding to the formula

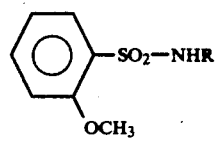

The Table shows for each compound the significance of the substituent R and the molecular-weight and melting-point characteristics for the crystallized form or forms isolated. The yields are given for the basic benzenesulphonamide.

| No. | R | | M.W. | M.P. (°C.) | Yield th. % |
|---|---|---|---|---|---|
| 1 | $-(CH_2)_2-N\begin{subarray}{l}CH_3\\CH_3\end{subarray}$ | picrate | 487,42 | 110 | 70 |
| 2 | $-(CH_2)_2-N\begin{subarray}{l}C_2H_5\\C_2H_5\end{subarray}$ | picrate base | 515,47 286,34 | 122 62 | 64 |
| 3 | $-(CH_2)_2-N\diagdown O\diagup$ | picrate | 529,46 | 148 | 61 |
| 4 | $-(CH_2)_2-N\diagdown\square\diagup$ | picrate base | 513,46 284,37 | 115 74 | 64 |
| 5 | $-(CH_2)_2-N\diagdown\bigcirc\diagup$ | picrate | 527,49 | 140 | 62 |
| 6 | $-(CH_2)_3-N\begin{subarray}{l}CH_3\\CH_3\end{subarray}$ | picrate | 501,45 | 138 | 67 |
| 7 | $-(CH_2)_3-N\begin{subarray}{l}C_2H_5\\C_2H_5\end{subarray}$ | picrate | 529,50 | 132 | 61 |
| 8 | $-(CH_2)_3-N\diagdown O\diagup$ | picrate | 543,48 | 115 | 59 |
| 9 | $-(CH_2)_3-N\diagdown\bigcirc\diagup$ | picrate | 541,51 | 158 | 59 |

EXAMPLE 2

Preparation of 2-methoxy-4-nitrobenzenesulphonyl chloride.

0.05 mol (8.6 g) of 2-methoxy-4-nitroaniline is dissolved in 17 ml of hydrochloric acid (d=1.18). The amine is diazotized at 0° C. by adding 3.8 g of sodium nitrite in solution in 17 ml of water.

Moreover, 2 g of cupric chloride dissolved in the minimum of water necessary are added to 40 ml of pure acetic acid; the solution is saturated in the cold state with sulphur dioxide.

The freshly prepared diazonium salt is poured slowly into the acetic solution while stirring. After the termination of the liberation of nitrogen, the reaction medium is diluted with ice water; the sulphonyl chloride precipitates; it is separated and dried.

Yield: 79%; M.P.=91° C.

When the diazotization is carried out, there remains a residue of undiazotized amine which must be eliminated, for example by decantation, in order to avoid secondary reactions with the sulphonyl chloride subsequently formed.

Preparation of the N-substituted 2-methoxy-4-nitrobenzenesulphonamides.

General method of operation:

0.1 mol of 2-methoxy-4-nitrobenzenesulphonyl chloride is dissolved in 150 ml of anhydrous benzene. 0.1 mol of the chosen amine is added drop by drop while stirring; the solution becomes hot and then cloudy; the sulphonamide hydrochloride formed is deposited in the form of a microcrystalline yellow powder. It is separated and then washed with two portions of 20 ml of ethyl ether.

If necessary, the reaction may be started by slight heating.

Yield obtained: 75 to 90% according to the amines.

Preparation of the N-substituted 2-methoxy-4-aminobenzenesulphonamides.

General method of operation:

0.01 mol of nitrated sulphonamide is suspended in 50 ml of absolute alcohol; 3 g of nickel prepared by the RANEY process are added; the mixture is hydrogenated at atmospheric pressure and at room temperature while stirring. The catalyst is separated and then washed with two portions of 10 ml of boiling ethanol. The alcoholic solution is concentrated; by adding ether, the hydrochloride crystallizes in the form of white needles.

Examples of N-substituted 2-methoxy-4-nitro- and 2-methoxy-4-aminobenzenesulphonamides prepared in the manner hereinbefore described are given in the following Table. These compounds have a general structure corresponding to the formula

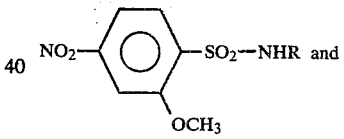 and

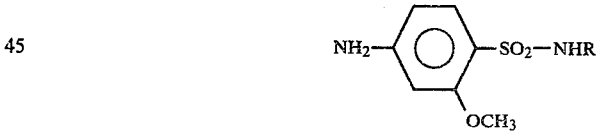

The Table shows, for each compound, the significance of the substituent R and the molar-weight and melting-point characteristics. For the nitro compounds, the melting point corresponds to the hydrochloride. For the amino compounds, the melting points are shown for the basic amide and the hydrochloride.

| | Nitro compounds: | | | |
|---|---|---|---|---|
| No. | R | M.W. base | M.P. (°C.) | Yield th % |
| 10 | $-(CH_2)_2-N\begin{subarray}{l}CH_3\\CH_3\end{subarray}$ | 339,5 | 152-6 | 88 |
| 11 | $-(CH_2)_2-N\begin{subarray}{l}C_2H_5\\C_2H_5\end{subarray}$ | 367,5 | 142-5 | 75 |

-continued

Nitro compounds:

| No. | R | M.W. base | M.P. (°C.) | Yield th % |
|---|---|---|---|---|
| 12 | —(CH₂)₂—N(morpholine) | 381,5 | 157-62 | 78 |
| 13 | —(CH₂)₂—N(pyrrolidine) | 365 | 128-32 | 90 |
| 14 | —(CH₂)₂—N(piperidine) | 379,8 | 144-8 | 88 |
| 15 | —(CH₂)₃—N(CH₃)₂ | 353,5 | 161-4 | 88 |
| 16 | —(CH₂)₃—N(C₂H₅)₂ | 381,5 | 155-9 | 80 |
| 17 | —(CH₂)₃—N(morpholine) | 395,5 | 157-62 | 78 |

Amino compounds:

| No. | R | M.W. base | M.P. (°C.) base | M.P. (°C.) hydrochloride |
|---|---|---|---|---|
| 18 | —(CH₂)₂—N(CH₃)₂ | 273,29 | 92 | 127,9 |
| 19 | —(CH₂)₂—N(C₂H₅)₂ | 301,28 | 115 | 128,30 |
| 20 | —(CH₂)₂—N(morpholine) | 299,32 | 163 | 180,4 |
| 22 | —(CH₂)₂—N(piperidine) | 313,35 | 169 | |
| 23 | —(CH₂)₃—N(CH₃)₂ | 287,31 | 122 | 162,5 |
| 24 | —(CH₂)₃—N(C₂H₅)₂ | 315,36 | 124 | 131 |
| 25 | —(CH₂)₃—N(morpholine) | 329,32 | 150 | |

EXAMPLE 3

Preparation of 4-chloro-2-nitrophenol 0.125 mol (16 g) of 4-chlorophenol, 25 ml of water and 35 ml of acetic acid are introduced into a 125 ml three-necked flask equipped with a stirring system and a thermometer; the mixture is brought to 40° C. and 14.2 ml of nitric acid (d=1.38) are then added drop by drop; the reactants are left in contact for 5 hours. The product is separated by filtration and is crystallized in the minimum of absolute alcohol.

Yield=98% th. M.P.=85° C.

Preparation of 4-chloro-2-nitroanisole.

0.072 mol (12.6 g) of 4-chloro-2-nitrophenol, 40 ml of acetone and 9.72 g of potassium carbonate are introduced into a 250 ml three-necked flask equipped with a stirring system, a thermometer and a condenser. The mixture is brought to 40° C. and 9.72 g of dimethyl sulphate are then added drop by drop; the mixture is heated under reflux for 5 hours; the potassium sulphate is separated; the acetone solution is concentrated under reduced pressure and the 4-chloro-2-nitroanisole is precipitated. It is separated and then crystallized in a water/acetone mixture.

Yield=85% th. M.P.=95° C.

Preparation of 2-amino-4-chloroanisole 0.037 mol (7 g) of 4-chloro-2-nitroanisole is dissolved in 100 ml of absolute alcohol and 3 g of nickel prepared by the RANEY process are added. The solution is hydrogenated at atmospheric pressure and at room temperature while stirring. The catalyst is separated and then washed with two portions of 20 ml of boiling ethanol. The alcoholic solution is concentrated under reduced pressure; the 2-amino-4-chloroanisole crystallizes.

Yield=80% th. M.P.=84° C.

Preparation of 2-acetamido-4-chloroanisole.

0.2 mol (31.5 g) of 2-amino-4-chloroanisole, 40 ml of absolute alcohol, 20 ml of acetic anhydride and a pinch of zinc powder are placed in a 150 ml flask; the solution is brought to reflux for 30 minutes. The reaction liquid is poured onto crushed ice. The product obtained is separated; it is crystallized in a methanol/water mixture (20/80).

Yield=93% th. M.P.=102° C.

This yield can be further improved by operating in a reducing medium.

Preparation of 2-acetamido-4-chloro-5-nitroanisole 168 ml of NORDHAUSEN sulphuric acid containing 20% of sulphur trioxide are placed in a 1000 ml three-necked flask and the acid is cooled to about +5° C. and then 0.42 mol (84 g) of 2-acetamido-4-chloroanisole is then added in small portions; a mixture consisting of 44.4 ml of nitric acid and 37.2 ml of fuming sulphuric acid is introduced drop by drop; the mixture is brought to room temperature and it is left in contact for 6 hours while stirring; it is poured over crushed ice; the product precipitates and is separated and then washed copiously with ice water.

Yield=68% th. M.P.=185° C.

In the course of this reaction, secondary products are formed; by washing the precipitate obtained with dilute alcohol, a product was isolated which, after treatment with potash in aqueous medium, was considered identica with 2-amino-4-chloroanisole.

Preparation of 2-amino-4-chloro-5-nitroanisole 0.5 mol (99.5 g) of 2-acetamido-4-chloro-5-nitroanisole and 125 ml of a solution of potassium hydroxide (140 g of KOH/100 ml of water) are introduced into a 500 ml flask; the mixture is brought to between 100° and 110° C. for one hour and three quarters; the product is dried without heating and washed with water.

Yield=81% th. M.P.=131° C.

Preparation of 5-chloro-2-methoxy-4-nitrobenzenesulphonyl chloride 0.1 mol (20.2 g) of 2-amino-4-chloro-5-nitroanisole is dissolved in 60 ml of hydrochloric acid (d=1.18). The amine is diazotized between 0° and +5° C. by adding 10 g of sodium nitrite in solution in 50 ml of water.

Moreover, 7 g of cupric chloride dissolved in the minimum amount of water are added to 100 ml of pure acetic acid; the solution is saturated in the cold state with sulphur dioxide.

The freshly prepared diazonium salt is poured slowly into the acetic solution while stirring. After the termination of the liberation of nitrogen, the reaction medium is diluted with ice water; the sulphonyl chloride precipitates and is separated and washed.

Yield=66% th. M.P.=100° C.

Preparation of the N-substituted 2-methoxy-5-chloro-4-nitrobenzenesulphonamides

General method of operation:

0.05 mol of 5-chloro-2-methoxy-4-nitrobenzenesulphonyl chloride is dissolved in 60 ml of benzene. 0.05 mol of the amine selected is added drop by drop; the solution becomes heated and then clouds; the hydrochloride of the sulphonamide which is formed is deposited in the form of a crystalline powder. This is separated and it is then washed with two portions of 10 ml of ethyl ether.

Yield obtained: 74 to 90% of the theoretical according to the amine.

Preparation of the N-substituted 2-methoxy-4-amino-5-chlorobenzenesulphonamides

General method of operation:

0.01 mol of nitrated sulphonamide is suspended in 50 ml of absolute alcohol and 3 g of nickel prepared by the RANEY process are added. The mixture is hydrogenated at atmospheric pressure and at room temperature while stirring. The catalyst is separated and then washed with two portions of 10 ml of alcohol diluted in equal proportions. The solution obtained is concentrated under reduced pressure; by adding ether, the hydrochloride crystallizes.

Examples of N-substituted 2-methoxy-5-chloro-4-nitro- and -4-aminosulphonamides prepared in the manner hereinbefore described are given in the following Table. These compounds have a general structure corresponding to the formula

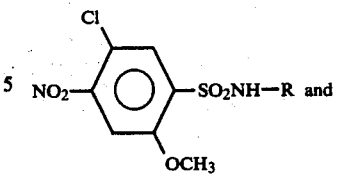

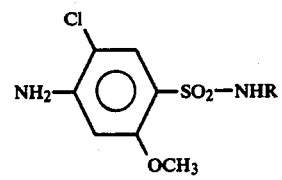

The Table shows for each compound the significance of the substituent R and the molar-weight, melting-point and yield characteristics corresponding to the hydrochloride.

Nitro compounds

| No. | R | M.W. | M.P.(°C.) | Yield % of th. |
|---|---|---|---|---|
| 26 | —(CH$_2$)$_2$—N(CH$_3$)$_2$ | 374,25 | 240 | 85 |
| 27 | —(CH$_2$)$_2$—N(C$_2$H$_5$)$_2$ | 402,30 | 219 | 80 |
| 28 | —(CH$_2$)$_2$—N(morpholino) | 379,82 | 214 | 88 |
| 29 | —(CH$_2$)$_2$—N(piperidino) | 414,32 | 198 | 90 |
| 30 | —(CH$_2$)$_3$—N(CH$_3$)$_2$ | 388,28 | 198 | 77 |
| 31 | —(CH$_2$)$_3$—N(C$_2$H$_5$)$_2$ | 416,33 | 182 | 81 |
| 32 | —(CH$_2$)$_3$—N(morpholino) | 430,29 | 208 | 78 |

Amino compounds

| Ref. | R | M.W. | M.P. (°C.) |
|---|---|---|---|
| 33 | —(CH$_2$)$_2$—N(CH$_3$)$_2$ | 344,25 | 145–8 |
| 34 | —(CH$_2$)$_2$—N(C$_2$H$_5$)$_2$ | 372,30 | 140 |

| Ref. | Amino compounds R | M.W. | M.P. (°C.) |
|---|---|---|---|
| 35 | —(CH₂)₂—N⟨O⟩ (morpholine) | 349,82 | 125–6 |
| 36 | —(CH₂)₂—N⟨ ⟩ (piperidine) | 384,32 | 137–9 |
| 37 | —(CH₂)₃—N(CH₃)₂ | 358,28 | 130–2 |
| 38 | —(CH₂)₃—N(C₂H₅)₂ | 386,33 | 140–1 |
| 39 | —(CH₂)₃—N⟨O⟩ (morpholine) | 400,31 | 160–2 |
| 40 | —(CH₂)₃—N⟨ ⟩ (piperidine) | | 160–5 |

EXAMPLE 4

Preparation of 5-chloro-2-methoxybenzenesulphonyl chloride 1 mol (66 ml) of chlorosulphonic acid is placed in a 250 ml three-necked flask equipped with a stirring system, a thermometer and a dropping funnel; cooling to about 10° C. is carried out and then 0.2 mol (29.8 g) of 4-chloroanisole is added drop by drop.

The addition having been completed, the mixture is brought to 60° C. for 2 hours. The solution obtained is poured onto crushed ice: the sulphonyl chloride precipitates in the form of a white powder.

Yield=68% th. M.P.=104° C.

0.13 mol (21 g) of 2-amino-4-chloroanisole is dissolved in 42 ml of hydrochloric acid (d=1.18). The amine is diazotized between 0° and +5° C. by adding 10 g of sodium nitrite in solution in 40 ml of water.

Moreover, 6 g of cupric chloride dissolved in the minimum amount of water are added to 150 ml of pure acetic acid; the solution is saturated in the cold state with sulphur dioxide.

The freshly prepared diazonium salt is poured slowly into the acetic solution while stirring. When the liberation of nitrogen has been completed, the solution is poured over crushed ice; the sulphonyl chloride precipitates.

Yield=46% th. M.P.=102° C.

Preparation of the N-substituted 2-methoxy-5-chlorobenzenesulphonamides

General method of operation:

0.05 mol of 5-chloro-2-methoxybenzenesulphonyl chloride is dissolved in 50 ml of chloroform; 0.05 mol of amine is added drop by drop; the reactants are left in contact for 1 hour. The hydrochloride of the sulphonamide which is formed is separated after precipitation. It is crystallized in ethanol.

Examples of N-substituted 2-methoxy-5-chlorobenzenesulphonamides prepared as described hereinbefore are given in the following Table. These compounds correspond to the formula:

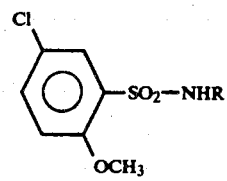

This Table shows, for each compound, the significance of the substituent R and the molar-weight and melting-point characteristics of the corresponding salt (hydrochloride or methane sulphonate).

| Ref. | R | | M.W. | M.P. (°C.) | Yield % of th. |
|---|---|---|---|---|---|
| 41 | —(CH₂)₂—N(CH₃)₂ | ,HCl | 329,24 | 247 | 79 |
| 42 | —(CH₂)₂—N(C₂H₅)₂ | ,CH₃SO₃H | 415,91 | 133–4 | 61 |
| 43 | —(CH₂)₂—N⟨O⟩ | ,HCl | 371,27 | 235 | 72 |
| 44 | —(CH₂)₂—N⟨ ⟩ | ,HCl | 355,27 | 171 | 90 |
| 45 | —(CH₂)₂—N⟨ ⟩ | ,HCl | 369,30 | 202 | 89 |
| 46 | —(CH₂)₃—N(CH₃)₂ | ,HCl | 343,26 | 202 | 75 |
| 47 | —(CH₂)₃—N(C₂H₅)₂ | base | 334,86 | 80 | 70 |
| 48 | —(CH₂)₃—N⟨O⟩ | ,HCl | 385,30 | 238 | 60 |

EXAMPLE 5

Preparation of 4-methoxy-5-nitrobenzenesulphonyl chloride 2.5 mols (165 ml) of chlorosulphonic acid are placed in a one-liter reaction vessel equipped with a stirring system, a thermometer and a dropping funnel and the acid is cooled to about 0° C. with a mixture of ice and salt. 0.8 mol (100 ml) of 2-nitroanisole is added drop by drop and the solution is then allowed to come back to room temperature; after a contact time of 30 minutes, the reaction mixture is poured onto one fifth of its volume of crushed ice. The sulphonyl chloride precipitates in the form of an oil; this is extracted with chloroform. After evaporation of the organic phase, the sulphonyl chloride is crystallized in a benzene/petroleum ether mixture.

Yield=40% th. M.P.=62° C.

Preparation of 4-methoxy-5-nitrobenzenesulphonamide 0.4 mol (63 g) of 4-methoxy-5-nitrobenzenesulphonyl chloride is dissolved in 250 ml of chloroform; the solution is cooled to about −5° C. and then a stream of ammonia is allowed to bubble in for 15 minutes. The sulphonamide obtained is precipitated; the ammonium chloride formed is separated by washing with ice water. The sulphonamide is crystallized in an alcohol/ether mixture.

Yield=81% th. M.P.=135° C.

Preparation of 3-amino-4-methoxybenzenesulphonamide 0.1 mol (23.2 g) of 4-methoxy-5-nitrobenzenesulphonamide is dissolved in 300 ml of absolute alcohol and 10 g of nickel prepared by the RANEY process are added. The solution is hydrogenated at atmospheric pressure and at room temperature while stirring. The catalyst is separated and then washed with two portions of 50 ml of alcohol; the solution is concentrated under reduced pressure; the 3-amino-4-methoxybenzenesulphonamide crystallizes.

Yield=85% th. M.P.=142° C.

Preparation of 2-methoxy-5-sulphamoylbenzenesulphonyl chloride 0.05 mol (10.1 g) of 3-amino-4-methoxybenzenesulphonamide is dissolved in 10 ml of hydrochloric acid (d=1.18) and 20 ml of water. The amine is diazotized between 0° and +5° C. by adding 4 g of sodium nitrite in solution in 20 ml of water.

Moreover, 3 g of cupric chloride dissolved in the minimum of water are added to 40 ml of pure acetic acid; the solution is saturated in the cold state with sulphur dioxide.

The freshly prepared diazonium salt is poured, after slight heating, into the acetic solution while stirring; the reactants are left in contact at about 35° C. for 30 minutes; the reaction medium is diluted with ice water. The sulphonyl chloride is allowed to precipitate in an ice box for 1½ hours; it is separated and then washed with ice water. It is crystallized in a dioxan/petroleum ether mixture.

Yield=36% th. M.P.=178° C.

Preparation of the N-substituted 2-methoxy-5-sulphamoylbenzenesulphonamides

General method of operation:

0.05 mol of 2-methoxy-5-sulphamoylbenzenesulphonyl chloride is suspended in 15 ml of chloroform. 0.05 mol of the amine selected, previously dissolved in 10 ml of absolute alcohol, is added drop by drop while stirring. Heating is observed and then the formation of gums.

Purification is obtained (1) By fractional crystallization.

The gums are separated and are then dissolved with the use of heat in ethanol; by successive addition of ether, the expected hydrochloride is obtained and crystallizes in the form of a microcrystalline powder.

(2) By chromatography on an alumina column:

Elution is effected with a chloroform/acetone mixture (95/5) and then with a chloroform/ethanol mixture (90/10).

Examples of N-substituted 2-methoxy-5-sulphamoylbenzenesulphonamides prepared as described hereinbefore are given in the following Table. These compounds correspond to the formula:

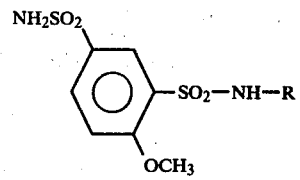

The Table shows, for each compound, the significance of the substituent R, the molar weight and the melting point.

| Ref. | R | | M.W | M.P. (°C.) |
|------|---|---|-----|------------|
| 49 | —(CH$_2$)$_2$—N(CH$_3$)$_2$ | hydrochloride | 373,86 | 140 |
| 50 | —(CH$_2$)$_2$—N(C$_2$H$_5$)$_2$ | hydrochloride | 401,91 | 145–6 |
| 51 | —(CH$_2$)$_2$—N(morpholino) | | 379,43 | 165 |
| 52 | —(CH$_2$)$_2$—N(piperidino) | | 377,46 | 158 |

The new compounds of the general formula (I) have pharmacological properties of great value. They are distinguished in particular by their antiemetic, local anesthetic and anticonvulsive properties. They are, moreover, antibiotic products. These compounds are moreover remarkable because of their low degree of toxicity.

Determination of toxicity

The acute toxicity of the compounds according to the invention was determined on male mice whose weight varied between 24 and 26 g. The compounds are administered intravenously in solution form and at the rate of 0.5 ml per 20 g of body weight, by varying the concentration of the injected solution.

Each compound is tested on a batch of 5 mice which are examined for 6 days following the injection.

It is found that the LD$_{50}$, for the majority of these compounds, is higher than 100 mg/kg, and, for all the compounds, higher than 50 mg/kg.

Determination of central antiemetic activity

These tests were carried out on adult Beagle dogs with a weight of 7 to 12 kg and which had gone without food for 18 hours. The dogs receive a dose of 1 mg/kg (0.1 ml/kg) of the compound according to the invention by intramuscular injection. 30 minutes later, 0.1 mg/kg (0.1 ml/kg) of apomorphine is administered to them subcutaneously as a central emetic compound. The vomitings during the 30 minutes following the injection of apomorphine are counted. For two dogs serving as controls and receiving only the apomorphine 22 vomitings were counted. It is found that the majority of the compounds tested have a certain antiemetic activity, in particular in the case of the compound of the general formula (II), and that this activity is even excellent in the case of some products, among them in particular the compound 2-methoxy-4-amino-5-chloro-N-(3-diethylaminopropyl)benzenesulphonamide. The results were confirmed by alternate tests by resuming these tests and interchanging the control dogs and the dogs on which the compounds according to the invention were previously tried.

The results relating to the toxicity and the central antiemetic activity of the compounds given hereinbefore are stated clearly in the following Table. The antiemetic activity is expressed in the form of the average number of vomitings for two dogs and is to be compared with the number 22 obtained with the control animals.

| Ref. | Compounds | Toxicity mg/kg | Antiemetic effect /22 |
| --- | --- | --- | --- |
| a | NO$_2$—C$_6$H$_3$(OCH$_3$)—SO$_2$—NH—(CH$_2$)$_2$—N(C$_2$H$_5$)$_2$ | 100 < — | 15 |
| b | NH$_2$—C$_6$H$_3$(OCH$_3$)—SO$_2$—NH—(CH$_2$)$_2$—N(C$_2$H$_5$)$_2$ | 100 < — | 22 |
| c | NH$_2$—C$_6$H$_3$(OCH$_3$)—SO$_2$—NH—(CH$_2$)$_2$—N(C$_2$H$_5$)$_2$ | 50 < — < 100 | 17 |
| d | Cl, NO$_2$—C$_6$H$_2$(OCH$_3$)—SO$_2$—NH—(CH$_2$)$_2$—N(piperidine) | 100 < — | 16 |
| e | Cl, NO$_2$—C$_6$H$_2$(OCH$_3$)—SO$_2$—NH—(CH$_2$)$_3$—N(C$_2$H$_5$)$_2$ | 100 < — | |
| f | Cl, NH$_2$—C$_6$H$_2$(OCH$_3$)—SO$_2$—NH—(CH$_2$)$_2$—N(C$_2$H$_5$)$_2$ | 50 < — < 100 | 13 |
| g | Cl, NH$_2$—C$_6$H$_2$(OCH$_3$)—SO$_2$—NH—(CH$_2$)$_2$—N(piperidine) | 50 < — < 100 | 13 |
| h | Cl, NH$_2$—C$_6$H$_2$(OCH$_3$)—SO$_2$—NH—(CH$_2$)$_3$—N(CH$_3$)$_2$ | 100 < — | 9 |
| i | Cl, NH$_2$—C$_6$H$_2$(OCH$_3$)—SO$_2$—NH—(CH$_2$)$_3$—N(C$_2$H$_5$)$_2$ | 117 | 3 |
| j | Cl, NH$_2$—C$_6$H$_2$(OCH$_3$)—SO$_2$—NH—(CH$_2$)$_3$—N(morpholine) | 100 < — | 22 |
| k | Cl—C$_6$H$_3$(OCH$_3$)—SO$_2$—NH—(CH$_2$)$_2$—N(CH$_3$)$_2$ | 100 < — | 22 |

-continued

| Ref. | Compounds | Toxicity mg/kg | Antiemetic effect /22 |
|---|---|---|---|
| l | Cl-C6H3(OCH3)-SO2—NH—(CH2)2—N(C2H5)2 | 100 < — | 8 |
| m | Cl-C6H3(OCH3)-SO2—NH—(CH2)3—N(C2H5)2 | insoluble | 12 |
| n | H2NO2S-C6H3(OCH3)-SO2—NH—(CH2)2—N(CH3)2 | 100 < — | |
| o | Cl-C6H2(NH2)(OCH3)-SO2—NH—(CH2)3—N(piperidine) | 80 < — < 100 | |

Local anesthetic activity

This activity was measured on the cornea of rabbits by Régnier's method, described in particular in "Principes de la pharmacodynamie," pp. 204–206, Masson (1959). The compounds 2-methoxy-4-amino-N-(2-diethylaminoethyl)benzenesulphonamide (b) and 2-methoxy-4-amino-N-(3-diethylaminopropyl)benzenesulphonamide (c) both showed a certain local anesthetic action.

Anticonvulsive activity

The compounds according to the invention were tested for their anticonvulsive activity by following the procedure described hereinafter.

Each compound is administered intraperitoneally to a batch of mice at the rate of 50 mg of compound per kilogram of body weight. 30 minutes later the mice receive, still intraperitoneally, 100 mg/kg of pentetrazole.

The time of appearance of the first convulsions (clonic convulsions), that of the tonic convulsions (hyperextension) and the death of the mice is then measured. The injections of pentetrazole are carried out comparatively on control animals.

In all cases, in mice treated with the compounds according to the invention, a considerable lengthening of the time of appearance of the three phenomena hereinbefore mentioned is found. In the case of the compound 2-methoxy-4-amino-5-chloro-N-(3-diethylaminopropyl)benzenesulphonamide (i), however, a decrease in the lethalness is found; three only of the five mice in the batch to which this compound was administered being dead at the end of this test.

Antibiotic activity

The bacteriostatic activity of the substances according to the invention was studied in particular on strains of pneumococci sensitive to sulphomethoxypyridazine. For these tests, pellets of filter paper 5 to 6 mm in diameter are impregnated with the substances according to the invention at the rate of 1/10 mg of active substance per pellet. The pellets prepared in this way and identified and control pellet are distributed on gelose contained in Petri dishes. The pellets are then submerged in a culture of pneumococci. The bacteriostatic activity is manifested by the formation of areas of lysis around the pellets impregnated with the substances according to the invention.

By reason of their remarkable pharmacological properties, the benzenesulphonamides according to the invention are of great interest as an active substance of medicaments for various kinds of therapeutics. In particular, they can be used:

(1) as antiemetics in the clinically observed pathological manifestations of the digestion, nausea, vomiting, painful syndromes, migraines;

(2) as a local anesthetic;

(3) as a depressive anticonvulsive agent for the central nervous system, in particular for nerve pathology in states of psychomotive excitation.

The medicaments containing the compounds according to the invention as active substances may be presented in very different pharmaceutical forms according to the treatment in question. For antiemetic or anticonvulsive treatments, administration may be effected orally in the form of tablets, lozenges, capsules, gelatin-coated pills, solutions and syrups, it being possible for solid or liquid adjuvants and excipients to complete the preparation. For these same treatments, administration may be effected by injection of the active substance in the form of solution in a sterile liquid medium. These medicaments may also be administered in the form of suppositories. For local anesthesia treatments, the medicament containing the substance may be presented in the form of ointments, lotions and collyria.

In all these medicaments, the compounds according to the invention may moreover be associated with other active substances.

By way of indication, the unit doses used for the compounds according to the invention range between about 10 and about 500 mg and preferably between 50 and 300 mg. The doses used are in accordance, in particular, with the method of administration chosen.

As is obvious and as is moreover already apparent from the foregoing, the invention is in no way limited to those modes of application and embodiments thereof which have been more especially considered; on the contrary, it covers all variants thereof.

We claim:
1. An N-substituted benzenesulphonamide wherein the benzene ring is substituted in the 2-position by a methoxy group, which has the following general formula (I)

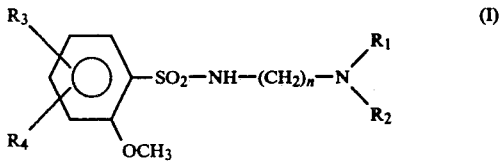

in which
n is 2 or 3
$R_1$ and $R_2$ jointly form with the nitrogen a heterocyclic ring having 5 or 6 members,
$R_3$ is a hydrogen atom, an $NO_2$ group, an $NH_2$ group or a halogen,
$R_4$ is a hydrogen atom, $NH_2$, a halogen or a sulphonamide group,
or the addition salts of (I) with a physiologically acceptable mineral or organic acid.

2. The benzenesulphonamide of claim 1, wherein $R_1$ and $R_2$ jointly form a heterocyclic ring selected from the group consisting of piperidino, pyrrolidino or morpholino.

3. The benzenesulphonamide of claim 2, wherein $R_1$ and $R_2$ jointly form piperidino.

4. The benzenesulphonamide of claim 2, wherein $R_1$ and $R_2$ jointly form pyrrolidino.

5. The benzenesulphonamide of claim 2, wherein $R_1$ and $R_2$ jointly form morpholino.

6. The benzenesulphonamide of claim 1, wherein n is 2.

7. The benzenesulphonamide of claim 1, wherein n is 3.

8. The benzenesulphonamide addition salts with a physiologically acceptable mineral or organic acid of claim 1.

9. A pharmaceutical antiemetic, anticonvulsive, local anesthetic or bacterostatic composition of low toxicity comprising a benzenesulphonamide of claim 1 in a therapeutically effective amount and a pharmaceutically acceptable carrier.

10. A pharmaceutical antiemetic, anticonvulsive, local anesthetic or bacterostatic composition of low toxicity comprising the benzenesulphonamide of claim 2 in a therapeutically effective amount and a pharmaceutically acceptable carrier.

11. A pharmaceutical antiemetic, anticonvulsive, local anesthetic or bacterostatic composition of low toxicity comprising the benzenesulphonamide of claim 3 in a therapeutically effective amount and a pharmaceutically acceptable carrier.

12. A pharmaceutical antiemetic, anticonvulsive, local anesthetic or bacterostatic composition of low toxicity comprising the benzenesulphonamide of claim 4 in a therapeutically effective amount and a pharmaceutically acceptable carrier.

13. A pharmaceutical antiemetic, anticonvulsive, local anesthetic or bacterostatic composition of low toxicity comprising the benzenesulphonamide of claim 5 in a therapeutically effective amount and a pharmaceutically acceptable carrier.

14. A pharmaceutically antiemetic, anticonvulsive, local anesthetic or bacterostatic composition of low toxicity comprising the benzenesulphonamide of claim 6 in a therapeutically effective amount and a pharmaceutically acceptable carrier.

15. A pharmaceutical antiemetic, anticonvulsive, local anesthetic or bacterostatic composition of low toxicity comprising the benzenesulphonamide of claim 7 in a therapeutically effective amount and a pharmaceutically acceptable carrier.

16. A pharmaceutical antiemetic, anticonvulsive, local anesthetic or bacterostatic composition of low toxicity comprising a benzenesulphonamide addition salt of claim 8 in a therapeutically effective amount and a pharmaceutically acceptable carrier.

17. A method of producing an antiemetic, anticonvulsive, anesthetic or antibiotic effect which comprises administering the composition of claim 9 to a warm-blooded animal in need of such treatment in a therapeutically effective amount.

18. The process of claim 17, wherein the administration is oral.